United States Patent [19]

Mori

[11] Patent Number: 4,724,214
[45] Date of Patent: Feb. 9, 1988

[54] APPARATUS FOR PHOTOSYNTHESIS

[76] Inventor: Kei Mori, 3-16-3-501, Kaminoge, Setagaya-ku, Tokyo, Japan

[21] Appl. No.: 455,692

[22] Filed: Jan. 5, 1983

[30] Foreign Application Priority Data

Jan. 16, 1982 [JP] Japan .................................. 57-5261
Jul. 13, 1982 [JP] Japan ................................ 57-121401

[51] Int. Cl.⁴ ..................... C12M 1/38; C12M 1/00; C12M 1/04; C12M 1/06
[52] U.S. Cl. .................................. 435/290; 435/287; 435/313; 435/315; 47/1.4
[58] Field of Search .............. 435/287, 257, 173, 313, 435/813, 315, 289, 290, 314; 47/1.4; 422/23, 24, 186, 80, 143; 261/87, 114.4, 121.1; 239/228, 237, 240; 250/435, 436; 350/96.15

[56] References Cited

U.S. PATENT DOCUMENTS

| | | | |
|---|---|---|---|
| 2,609,277 | 9/1952 | McNamara | 261/114 VT |
| 2,658,310 | 11/1953 | Cook | 435/257 X |
| 2,777,677 | 1/1957 | Bunch | 261/121 R |
| 2,815,607 | 12/1957 | Schroeder | 435/257 X |
| 3,400,051 | 9/1968 | Hofschneider | 435/315 X |
| 3,782,701 | 1/1974 | Hunt | 261/87 |
| 3,959,923 | 6/1976 | Selke | 435/287 X |
| 3,986,297 | 10/1976 | Ichimura et al. | 47/1.4 |
| 4,087,936 | 5/1978 | Savins et al. | 47/1.4 |
| 4,676,956 | 6/1987 | Mori | 435/313 X |

FOREIGN PATENT DOCUMENTS

| | | | |
|---|---|---|---|
| 0118581 | 10/1978 | Japan | 435/313 |
| 0000282 | 5/1979 | PCT Int'l Appl. | 435/287 |
| 0000448 | 2/1983 | PCT Int'l Appl. | 435/287 |
| 1335546 | 12/1971 | U.S.S.R. | 47/1.4 |
| 0505405 | 5/1976 | U.S.S.R. | 47/1.4 |
| 0783340 | 11/1980 | U.S.S.R. | 47/1.4 |

Primary Examiner—Robert J. Warden
Assistant Examiner—Randall E. Deck
Attorney, Agent, or Firm—Jordan and Hamburg

[57] ABSTRACT

A photosynthetic reaction bath has thereinside a number of photoradiators in the form of narrow upright tubes. A baffle plate is disposed below the photoradiators and is formed with a number of apertures therethrough in a predetermined area thereof which may be a radially central area or a generally annular peripheral area. $CO_2$-containing air is fed into the reaction bath through the apertures in the baffle plate to circulate along a predetermined path inside the reaction bath due to the remaining non-apertured part of the baffle plate. The function of the baffle plate may be performed by plugging which blocks the passage of the air through the spacings between the lower ends of the adjacent photoradiators in the predetermined area. The circulation of the air may be caused more positively along a variable path by a rotor which is positioned below the photoradiators and rotatable by ejecting the air while supplying it to the interior of the reaction bath. The rotor is cushioned and supported by the air ejected therefrom during operation.

34 Claims, 11 Drawing Figures

APPARATUS FOR PHOTOSYNTHESIS

BACKGROUND OF THE INVENTION

The present invention relates to an apparatus for effectively photosynthesizing photosynthetic substances such as algae typified by chlorella or spirolina, photosynthetic bacteria or artificial photosynthetic substances such as callus.

Photosynthetic apparatuses heretofore proposed include an apparatus for culturing chlorella (unicellular microorganism containing chlorophyl). Difficulty experienced in culturing chlorella is that illumination with intensities higher than a certain level destroys the chlorophyl and produces a toxin (phaeophorbite) while illumination with intensities lower than a certain level fails to cause photosynthesis altogether. It is therefore a primary requisite for effective photo-synthesis that all the cells containing a photosynthetic substance be constantly supplied with light evenly distributed. Generally, organisms in a swarm increase not only their multiplying ability per unit volume but their resistance to other fungi. The culturing efficiency, therefore, grows poor unless a predetermined light radiating area per one liter of culture medium is ensured. With this in view, it has been customary to promote the transmission of light by reducing the number of individuals of a photosynthetic substance. This involves an inconsistency, however, because an increase in the number of individuals lowers the transmissibility to light and, therefore, requires collection of the individuals, but the resulting decrease in the number of individuals weakens the resistance to the fungi. Another drawback hitherto encountered is that the light intensity is excessively high for the individuals near a light source but is insufficient for those remote from the light source and, additionally, the light is absorbed by water to have its wavelength component varied. An ideal situation is, therefore, that a photosynthetic substance be passed through a very narrow clearance while a predetermined intensity of light is directed perpendicular to the clearance. Then, sufficient light will be evenly applied to all the cells containing the photosynthetic substance with a minimum of attenuation and without any change in its wavelength component.

A photosynthetic apparatus presently in use includes a number of fluorescent lamps arranged in a reaction bath (e.g. chlorella culturing bath) and causes a photosynthetic substance to flow through the spaces between the lamps. However, the use of fluorescent lamps renders the apparatus bulky, increases power consumption and requires an awkward measure against heat generation by the lamps.

While the even supply of a sufficient amount of carbon dioxide ($CO_2$) all over the reaction bath is essential in attempting efficient photosynthesis, it has been quite difficult so far to fulfill such a condition.

Additionally, no effective means has been proposed for preventing contamination by the dead part of a photosynthetic substance or the like which tends to accumulate in various sections of a reaction bath.

SUMMARY OF THE INVENTION

An apparatus for photosynthesis embodying the present invention includes a photosynthetic reaction bath and a plurality of tubular photoradiators arranged upright in the reaction bath in parallel with each other. The reaction bath is communicated to a source of $CO_2$-containing air supply. A circulation means is provided for circulation in the reaction bath the $CO_2$-containing air which is fed from the conduit into the reaction bath.

In accordance with the present invention, a photosynthetic reaction bath has thereinside a number of photoradiators in the form of narrow upright tubes. A baffle plate is disposed below the photoradiators and is formed with a number of apertures therethrough in a predetermined area thereof which may be a radially central area or a generally annular peripheral area. $CO_2$-containing air is fed into the reaction bath through the apertures in the baffle plate to circulate along a predetermined path inside the reaction bath due to the remaining non-apertured part of the baffle plate. The function of the baffle plate may be performed by plugging which blocks the passage of the air through the spacings between the lower ends of the adjacent photoradiators in the predetermined area. The circulation of the air may be caused more positively along a variable path by a rotor which is positioned below the photoradiators and rotatable by ejecting the air while supplying it to the interior of the reaction bath. The rotor is cushioned and rotatably supported by the air ejected therefrom during operation.

It is an object of the present invention to provide an apparatus for photosynthesis which enhances the efficiency of photosynthetic reaction.

It is another object of the present invention to provide an apparatus for photosynthesis which sets up an even distribution of $CO_2$-containing air for all the cells in a reaction bath.

It is another object of the present invention to provide an apparatus for photosynthesis which automatically keeps its interior clean for a long period of time to facilitate services.

It is another object of the present invention to provide a generally improved apparatus for photosynthesis.

Other objects, together with the foregoing, are attained in the embodiments described in the following description and illustrated in the accompanying drawings.

DESCRIPTION OF THE PREFERRED EMBODIMENTS

While the apparatus for photosynthesis of the present invention is susceptible of numerous physical embodiments, depending upon the environment and requirements of use, substantial numbers of the herein shown and described embodiments have been made, tested and used, and all have performed in an eminently satisfactory manner.

Figure 1:
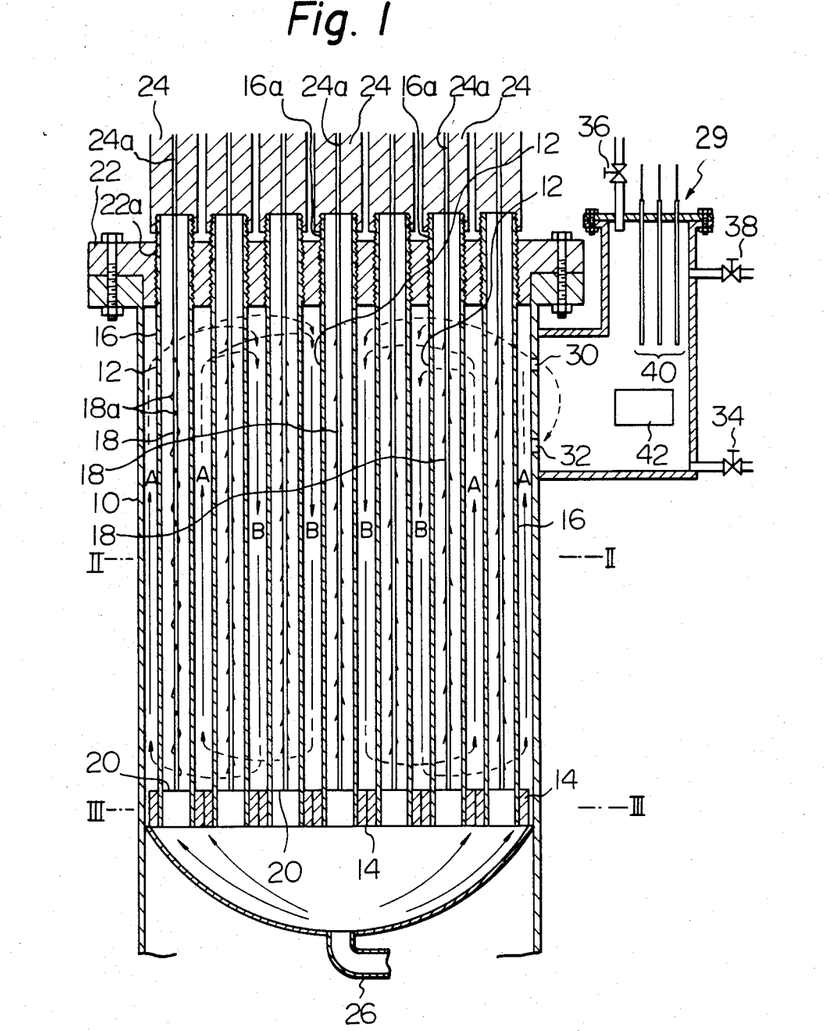
FIG. 1 is a sectional side elevation of an apparatus for photosynthesis embodying the present invention.
Figure 2:
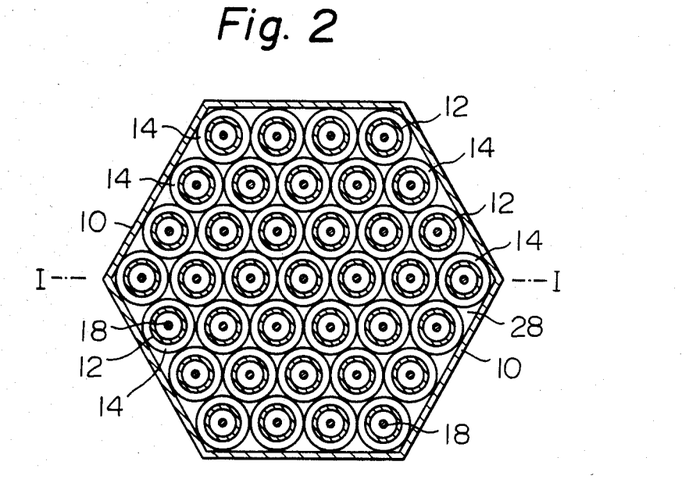
FIG. 2 is a section along line II—II of FIG. 1.
Figure 3:
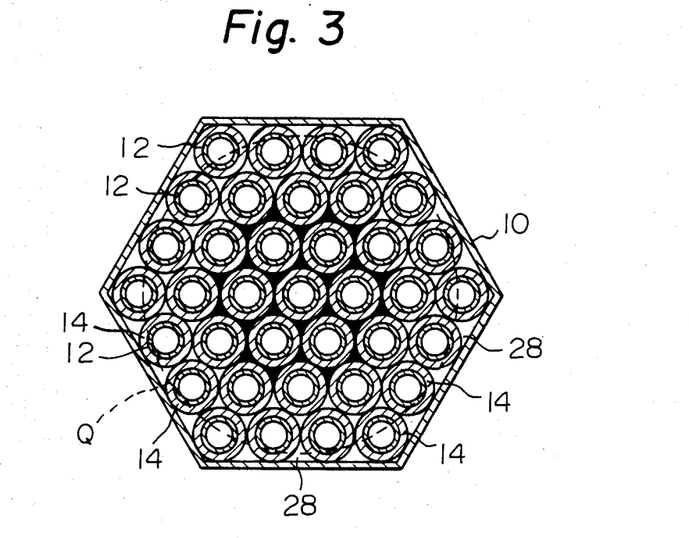
FIG. 3 is a section along line III—III of FIG. 1.

Referring to FIGS. 1-3 of the drawings, the photosynthetic apparatus includes a bath means or reaction bath which is generally designated by the reference numeral 10. A number of photoradiators 12 in the form of narrow tubes are arranged upright and in parallel with each other within the reaction bath 10. Each of the photoradiators 12 is rigidly fit in a short tube 14 at its lower end in a fluid tight manner. The photoradiator 12 comprises a transparent tube or sheath 16, an optical rod 18 and a mirror 20 located at a lower end portion of each photoradiator 12. A lid 22 removably covers the top of the reaction bath 10 and has threaded openings 22a in which threaded upper portions 16a of the respective tubes 16 are engaged. Thus, when the lid 22 is removed from the reaction bath 10, it is accompanied by the photoradiators 12 to facilitate cleaning of the reaction bath 10 or the photoradiators 12. Fiber optic cables 24 are in threaded engagement respectively with the upper ends of the threaded portions 16a of the tubes 16 at their light output ends. In this position of each cable 24, its optical fiber 24a is aligned at its end with the end of the optical rod 18 in the associated photoradiator 12, so that the light propagating through the optical fiber 24a is effectively transferred to the optical rod 18.

Each optical rod 18 is made of quartz, plastics or the like. The rod 18 carries thereon a light diffusing material 18a at desiredly spaced locations along its length. The light diffusing material 18a has a refractive index which is larger than that of quarts or plastics, thereby causing the light to break through the material 18a out of the rod 18.

A conduit 26 is communicated with the reaction bath 10 to supply $CO_2$-containing air thereinto. As shown in FIG. 3, the short tubes 14 in which the lower ends of the photoradiators 12 are fit are bonded together at their outer surfaces while defining gaps 28 therebetween. In the illustrated embodiment, the gaps 28 are stopped up by plug members in a central area of the reaction bath 10 (black gaps 28 in FIG. 3). $CO_2$-containing air fed into the reaction bath 10 by the conduit 26 flows through the open gaps 28 adjacent to the periphery of the bath 10, advances upward through the spaces between the photoradiators 12 as indicated by arrow A in FIG. 1, flows toward the center of the bath 10 at the upper end of the latter, flows down along the center as indicated by arrows B, and is then redirected by the closed gaps 28 in the central area toward the periphery of the reaction bath 10, thus circulating within the reaction bath 10. With this arrangement, the circulating air moves at a substantial velocity along the outer periphery of each photoradiator 12 while entraining the culture medium, thereby preventing the photosynthetic substance from becoming deposited on the photoradiators 12. This frees the output light of the photoradiators 12 from interception to thereby supply all the photosynthetic substance with optical energy and $CO_2$ each in an even distribution.

It will be seen in the above embodiment that, if the area is made smaller at the region where the air flows downward than at the region where the air flows upward, the velocity of water will be increased at the downward flow region to minimize contamination to the photoradiators 12 in this region. While the gaps 28 in the central area of the bath 10 are stopped up in the illustrated embodiment, those in the peripheral area may be stopped up instead.

An auxiliary bath 29 is mounted on an upper side portion of the reaction bath 10 and communicated with the latter through openings 30 and 32 which are located one above the other. A valve 34 is positioned in the vicinity of the lower end of the auxiliary bath 28 so as to discharge the product of photosynthesis from the apparatus. A second valve 36 is mounted on the top of the auxiliary bath 29. This valve 36 is operable to supplement the culture medium and pH control solution to make up for the shortage which results from the discharge of the product through the valve 34. A third valve 38 is mounted on an upper side portion of the auxiliary bath 29 in order to controllably let the air out of the reaction bath 10 to control the pressure inside the reaction bath 10. Where use is made of a pressure regulating valve as the valve 38 for automatically controlling the bath pressure to a reference level, the $CO_2$ concentration in the water can be increased to promote photosynthesis and, at the same time, the pressure in the reaction bath 10 is prevented from lowering to change $CO_2$ into $M^IHCO_3$. Disposed inside the auxiliary bath 29 are various instruments 40 for monitoring the photosynthetic reaction in the reaction bath 10, e.g. thermometer, pressure gauge, pH meter and densitometer. The conditions inside the reaction bath 10 are so controlled as to effect photosynthesis in an optimum manner in response to outputs of such instruments. For example, the temperature in the reaction bath 10 may be controlled by controlling a heat generating/absorbing device 42 which is positioned in the auxiliary bath 29. Also, the outputs of the instruments are processed to notify the timing to collect the product.

As long as the photosynthetic reaction is to be carried out without interruption, the product will be collected through the auxiliary bath 29. When interruption of the reaction is permissible, the end (not shown) of the conduit 26 may be communicated to a vacuum source (not shown) or the like instead of the $CO_2$-containing air supply, so that the product can be collected through the conduit 26.

Figure 4:
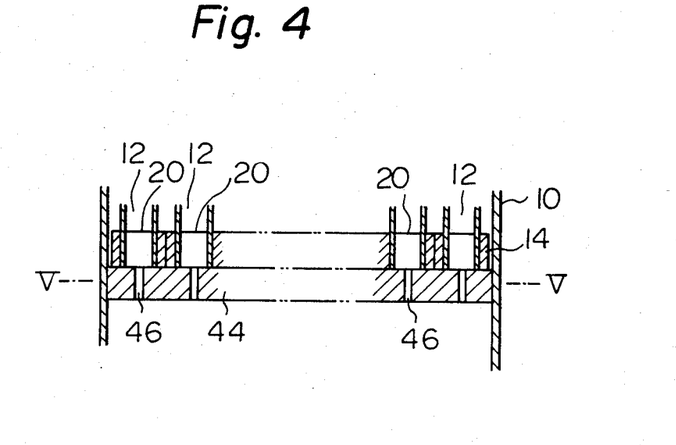
FIG. 4 is a fragmentary sectional side elevation of another embodiment of the present invention.
Figure 5:
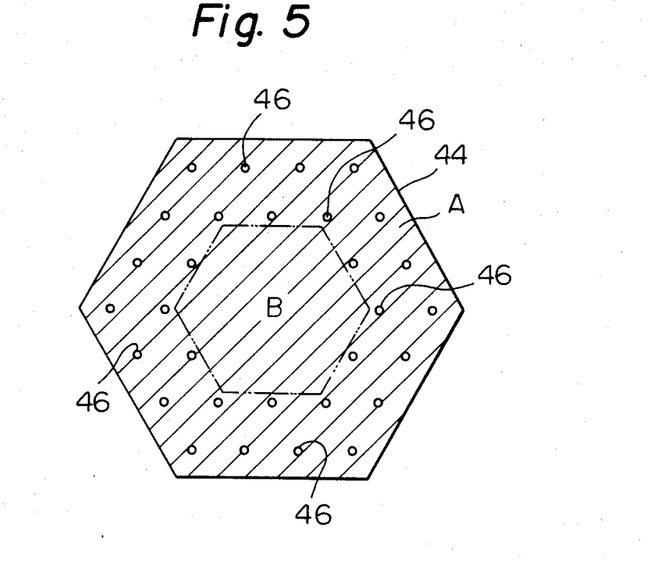
FIG. 5 is a section along line V—V of FIG. 4.

Referring to FIGS. 4 and 5, another embodiment of the present invention is shown which makes it needless to stop up the selected gaps 28 between the adjacent photoradiators 12. As previously described, the lower ends of the photoradiators 12 are respectively fit fluid-tight in the short tubes 14. The reference numeral 44 designates a baffle plate or obstruction plate which is rigidly supported by the reaction bath 10 in intimate contact with the bottoms of the photoradiators 12. The baffle plate 44 is formed with apertures 46 in its predetermined region A (corresponding to the region in FIG. 3 which does not contain the stopped-up gaps 28) and in positions corresponding to the gaps 28. The remaining region B of the baffle plate 44 is not formed with such apertures. In operation, the $CO_2$-containing air coming in through the conduit 26 is passed through the apertures 46 in the baffle plate 44 and caused to circulate in the reaction bath 12 in the manner described with reference to FIGS. 1-3. Thus, the baffle plate 44 eliminates the necessity of the operation for plugging the selected gaps 28 in the desired area, thereby cutting down the production cost of the apparatus.

Figure 6:
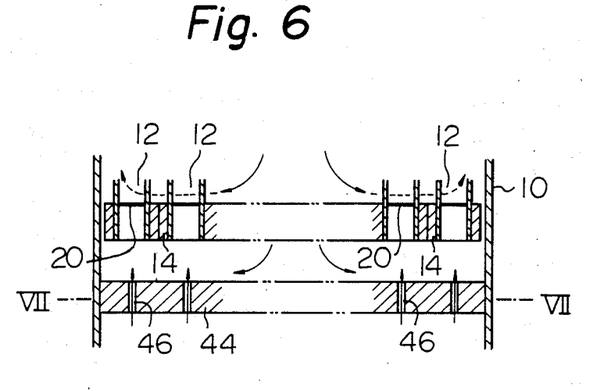
FIG. 6 is a view similar to FIG. 4 but showing another embodiment of the present invention.
Figure 7:
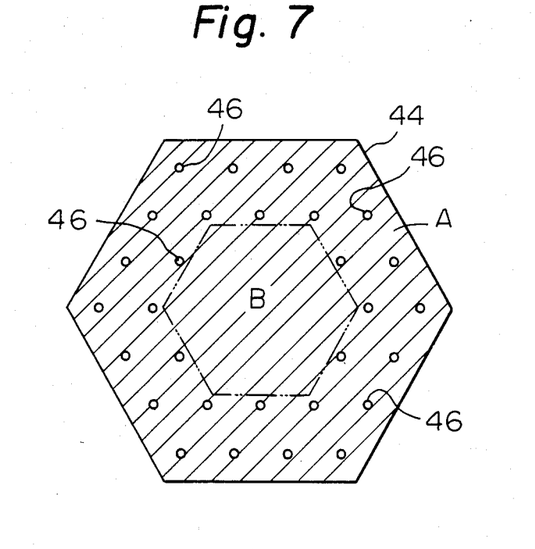
FIG. 7 is a section along line VII—VII of FIG. 6.
Figure 8:
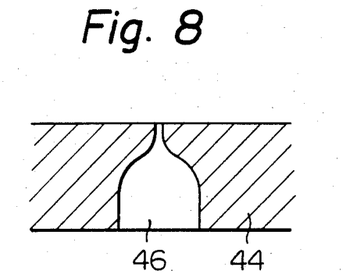
FIG. 8 and 9 are sectional side elevations showing different examples of a check valve mechanism applicable to the present invention.
Figure 9:
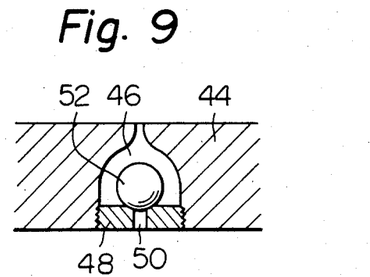

Referring to FIGS. 6 and 7, another embodiment of the present invention is shown which is essentially similar to the embodiment of FIGS. 4 and 5 but different therefrom in the position of the apertured baffle plate 44. As shown, the baffle plate 44 formed with the apertures 46 are supported by the reaction bath 10 at a predetermined spacing from the lower ends of the photoradiators 12. The apertures 46 are formed through the baffle plate 44 in the same region A as in the embodiment shown in FIGS. 4 and 5. In this construction, the air supply through the conduit 26 causes part of the downwardly flowing culture medium to circulate radially outward through the gaps between the photoradiators 12. However, the rest of the culture medium is allowed to flow straight onto the baffle plate 44 and then circulate radially outward through the clearance between the bottoms of the photoradiators 12 and the baffle plate 44. This reduces the contamination to the upper end portions of the short tubes 14. Where the baffle plate 44 is spaced apart from the bottoms of the photoradiators 12 as in the embodiment shown in FIGS. 6 and 7, the photoradiators 12 may be arranged in intimate contact with each other without using the short tubes 14, in order to substantially eliminate the contamination to the outer walls of the photoradiators 12. In this case, it is necessary to make the diameter of each photoradiator 12 smaller at the upper end than the lower end so that a passage is defined for the culture medium flow upward along the periphery (or the center) of the reaction bath 10 to be circulated toward the center (or the periphery).

Where the baffle plate 44 is employed in the position shown in FIGS. 4 and 5 or in the position shown in FIGS. 6 and 7, the diameter of the apertures 46 may be determined to allow the culture medium to pass therethrough so that the product can be collected through the conduit 26 (FIG. 1) by the vacuum source or the like (not shown). Alternatively, the apertures 46 may be provided with a diameter which passes air therethrough but not the culture medium. FIGS. 8 and 9 illustrate other possible implements for allowing the air to pass through the apertures 46 into the reaction zone, while checking the culture medium in the reaction zone. In FIG. 8, each aperture 46 is generally tapered toward the reaction zone. In FIG. 9, a valve seat member 48 having a passageway 50 is threaded into each aperture 46 which is tapered as in the configuration of FIG. 8. The valve seat 48 coacts with a ball 52 movably received in the aperture 46. In any case, the aperture 46 furnished with such a checking function prevents the conduit 26 from being stopped up by the culture medium or the like.

Figure 10:
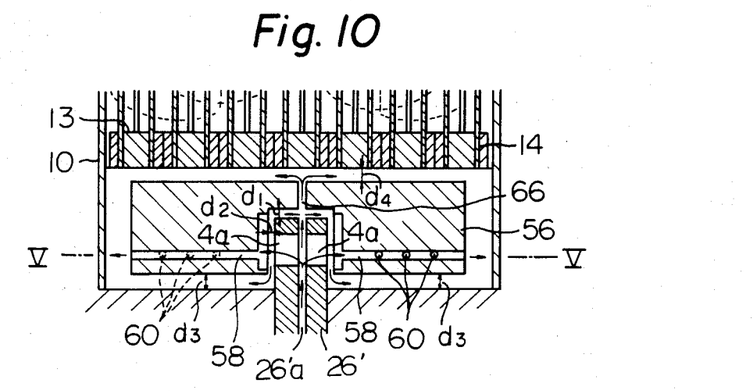
FIG. 10 is a fragmentary sectional side elevation of still another embodiment of the present invention.
Figure 11:
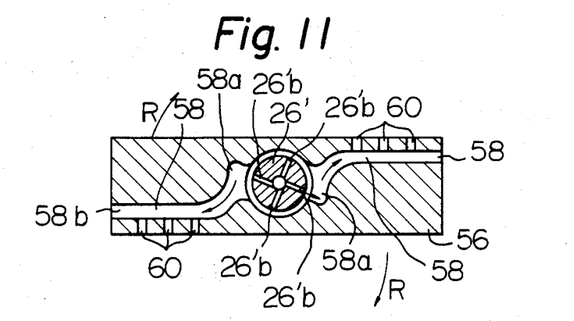
FIG. 11 is a section along line V—V of FIG. 10.

Referring to FIGS. 10 and 11, a further embodiment of the present invention is shown which is designed to achieve more efficient and positive recirculation of the culture medium within the reaction bath 10. In this embodiment, the conduit 26 (FIG. 1) has an extension 26' which protrudes into the reaction bath 10 to a position below the photoradiators 12. The conduit extension 26' is shaped at its upper end portion to have an axial passageway 26'a and a plurality of radial passageways 26'b which extend obliquely and radially outwardly from the axial passageway 26'a. A rotor 56 is movably coupled over the top of the conduit extension 26'. The rotor 56 is formed with passageways 58 and a plurality of air ejection ports 60 which extend throughout the rotor 56 from each of the passageway 58 as illustrated.

In operation, air fed through the axial passageway 26'a of the conduit extension 26' is discharged from the radial passageways 26'b to impinge on side wall portions 58a of the respective passageways 58, thereby giving the rotor 56 the tendency to rotate clockwise as indicated by arrows R in FIG. 11. The air passed through the passageways 58 are ejected from the ejection ports 60 to drive the rotor 56 in the direction R. The rotor 56 is caused to float by the air coming out through the upper end of the axial passageway 26'a of the conduit extension 26', a clearance $d_1$ thus developing between the upper end of the conduit extension 26' and the rotor 56. This part of the air, therefore, flows radially outward through the clearance $d_1$ as indicated by arrows in FIG. 10. Meanwhile, the air flowing through the gap $d_1$ and the air discharged from the radial passageways 26'b is partly routed through an annular clearance $d_2$ between the outer surface of the conduit extension 26' and the inner wall of the rotor 30 into a clearance $d_3$ between the bottom of the rotor 56 and the bottom of the reaction bath 10. As a result, the air streams in the clearances $d_1$ and $d_3$ serve as an air cushion for supporting the rotor 56 while the air stream in the clearance $d_2$ functions as an air bearing for rotatably supporting the rotor 56. The major torque acting on the rotor 56 is created by the air jets from the ejection ports 60. If desired, the rotor 56 may be formed with a through upward passageway 62 to pass the air into a clearance $d_4$ between the bottoms of the photoradiators 12 and the top of the rotor 56. The air stream in this clearance $d_4$ will more effectively air-cushion the rotor 56 in cooperation with the other air streams.

The embodiment described above with reference to FIGS. 10 and 11 achieves various advantages. Because the rotation of the rotor 56 affects the pneumatic pressure distribution in the bottom section of the reaction bath 10, the air circulation path in the reaction bath 10 progressively changes moment by moment. This as a whole distributes $CO_2$-containing air uniformly to all the air stream paths and, thereby, causes the reaction to occur more effectively. The culture medium, photosynthetic substance and the like falling toward the bottom of the reaction bath 10 are entrained upwardly by the air jets from the ejection ports 60, whereby dead part of the photosynthetic substance or the like is prevented from accumulating in the bottom of the reaction bath 10. If any such undesired accumulation is anticipated, the ejection ports 60 may be directed somewhat downwardly so that the accumulation will be scattered upwardly by the air jets. The bottom of the reaction bath 10 can thus be maintained clean for a long time. While the rotor 56 has been shown and described as being rotatably supported by the air bearing and air cushioning, use may be made of an ordinary mechanical bearing for the same purpose. The air bearing is still advantageous over the mechanical bearing because the rotor 56 needs only be placed between the conduit 26 and the photoradiators 12 and, therefore, it can be readily mounted and demounted to facilitate services.

Where the reaction bath 10 is formed not circular but polygonal such as hexagonal as in the foregoing embodiments, the passageways 58 formed in the rotor 56 may be extended to eject the air radially outward from the ends 58b of the rotor 56 and thereby effectively direct the air to the gaps 28 adjacent to the periphery of the reaction bath 10. Supposing that the outermost end of the rotor 56 move along the locus indicated by a dotted circle Q in FIG. 3, the resistance to the air ejection is larger when the ports 58b are in the positions a close to the wall of the reaction bath 10 than when they are in the positions b remote from the bath wall. The air, therefore, can be supplied substantially evenly to the air passages in both sections a and b. The rotor 56 may be formed with air ejection ports which are directed upwardly toward the photoradiators 12, thereby forcibly causing the air to flow through the gaps 28 in accordance with the movement of the rotor 56. Furthermore, the forced circulation of air makes it needless to plug the selected gaps 28 (see FIG. 3).

In summary, it will be seen that the present invention provides an apparatus for photosynthesis which promotes efficient photosynthetic reaction despite its simple and compact construction. Also, the apparatus can be kept clean over a long period of time to facilitate maintenance and inspection.

Various modifications will become possible for those skilled in the art after receiving the teachings of the present disclosure without departing from the scope thereof. For example, each photoradiator 12 may have a structure whose refractive index is larger in a peripheral section than in a central section, omitting the light diffusing material 12a shown in FIG. 1. In this connection, the use of rod-shaped optical conductors 18 as in FIG. 1 ensures linearity and facilitates their installation in the photoradiators 12. Two or more optical fibers 24a may be accommodated in each fiber optic cable 24; at least one of the optical fibers may be supplied with converged sunlight and at least one of the rest with artificial light. This allows the natural and artificial light to be used selectively: only the sunlight when it is intense, both the sunlight and artificial light in the morning and evening as well as in cloudy weather, and only the artificial light when the sunlight is unavailable at all as in the night. The cross-section of the tubes 16 of the photoradiators 12 is not limited to the illustrated circle but may be a polygon such as a triangle, a square or a hexagon. Likewise, the hexagonal cross-section of the reaction bath 10 is not restrictive but may be replaced with any other desired one.

I claim:

1. Apparatus for photosynthesis comprising bath means containing a photosynthetic reaction bath, a plurality of tubular photoradiators arranged upright in said bath means in parallel array, upper support means and lower support means in said bath means for supporting the upper and lower end portions respectively of said tubular photoradiators, said tubular photoradiators being spaced from one another so as to define a plurality of upright passages between said tubular photoradiators, said upper support means closing off the upper ends of said upright passages, said bath means having a lower chamber underlying said lower support means, said lower support means having a flow-through portion which provides communication between said chamber and a first plurality of upright passages and a stopped up portion which blocks communication between said chamber and a second plurality of upright passages, conduit means leading to said chamber for supplying $CO_2$-containing air, said flow-through portion and said stopped up portion of said lower support means being constructed and arranged such that said air passes from said chamber through said flow-through portion into said first plurality of upright passages, said air passing upwardly in said first plurality of upright passages and subsequently being directed generally laterally by said upper support means such that the air then passes downwardly in said second plurality of upright passages to subsequently again be directed generally laterally by said stopped up portion of said lower support means to once again pass upwardly in said first plurality of upright passages, whereby the air circulates in said bath means between said tubular photoradiators.

2. An apparatus as claimed in claim 1 further comprising circulation means causing the air to recirculate along a variable path in the bath means 3. An apparatus as claimed in claim 2 in which the circulation means comprises a circulation member which varies the circulation path by varying the pneumatic pressure distribution in a bottom portion of the bath means.

4. An apparatus as claimed in claim 1 further comprising an auxiliary bath communicating with an upper portion of the bath means.

5. An apparatus as claimed in claim 4, in which the auxiliary bath is communicated with the bath means by at least two vertically spaced ports.

6. An apparatus as claimed in claim 4 in which the auxiliary bath is formed with a product outlet at a lower end portion thereof and an air outlet and a culture medium inlet at an upper portion thereof.

7. An apparatus as claimed in claim 6, in which a pressure regulator valve is associated with the air outlet for automatically regulating the pressure inside the bath means.

8. An apparatus as claimed in claim 4, further comprising a heat generating and absorbing unit disposed in the auxiliary bath for controlling the temperature inside the bath means.

9. An apparatus as claimed in claim 1, in which each of the photoradiators comprises a transparent tubular sheath, an optical rod extending through said tubular sheath, and a light diffusing means for diffusing light transmitted through said optical rod to the outside into the bath means.

10. An apparatus as claimed in claim 9, in which the light diffusing means comprises a light diffusing material carried on the optical rod at spaced locations along the length of the rod.

11. An apparatus as claimed in claim 9, further comprising fiber optic cables each having at least two optical fibers thereinside and optically connected with the optical rod in one of the photoradiators, at least one of the optical fibers being supplied with converged sunlight and at least one of the other optical fibers being supplied with artificial light.

12. An apparatus as claimed in claim 1, further comprising mirror means at the lower end of each of the photoradiators.

13. An apparatus as claimed in claim 1 wherein said upper support means comprises a lid which removably covers the upper end of the bath means, the photoradiators being mounted fluid-tight on the lid at upper end portions thereof.

14. An apparatus as claimed in claim 1, wherein said lower support means comprises a plurality of tubes having an axial length shorter than the axial length of said tubular photoradiators, said tubular photoradiators having lower end portions fitted fluid-tightly to the insides of said tubes, said upright passages each having a lower portion and an upper portion, said lower portion being defined by said tubes, said upper portion being defined by said tubular photoradiators.

15. An apparatus as claimed in claim 14, wherein said stopped up portion of said lower support means comprises plug means disposed between said tubes, said plug means thereby closing off the lower ends of said second plurality of upright passages.

16. An apparatus as claimed in claim 14, wherein said lower support means further comprises a baffle plate underlying said plurality of tubes, said baffle plate having a plurality of apertures defining said flow-through portion, said baffle plate having a non-apertured portion defining said stopped up portion.

17. An apparatus as claimed in claim 16, wherein said lower support means comprises bonding means bonding said tubes to one another.

18. An apparatus as claimed in claim 16, wherein said lower support means comprises bonding means bonding said tubes to one another at tangential points of contact, said tubes each having a lower longitudinal end coincident with the lower longitudinal end of the respective photoradiator.

19. An apparatus as claimed in claim 18, wherein said baffle plate engages the lower ends of said tubes and photoradiators.

20. An apparatus as claimed in claim 1, wherein said stopped up portion is disposed at a generally radially central area of said bath means.

21. An apparatus as claimed in claim 20, wherein said flow-through portion is disposed at a generally annular area adjacent the periphery of said bath means, said flow-through portion being larger than said stopped up portion.

22. An apparatus according to claim 1, wherein said stopped up portion is disposed at a generally annular area adjacent the periphery of said bath means.

23. An apparatus according to claim 22, wherein said flow-through portion is disposed at a generally radially central area of said bath means, said flow-through portion being larger than said stopped up portion.

24. Apparatus for photosynthesis comprising bath means containing a photosynthetic reaction bath, a plurality of tubular photoradiators arranged upright in said bath means in parallel array, upper support means and lower support means in said bath means for supporting the upper and lower end portions respectively of said tubular photoradiators, said tubular photoradiators being spaced from one another so as to define a plurality of upright passages between said tubular photoradiators, said upper support means closing off the upper ends of said upright passages, a baffle plate underlying said lower support means, said bath means having a lower chamber underlying said baffle plate, said baffle plate having a plurality of apertures providing communication between said chamber and a first plurality of upright passages, said baffle plate having a non-apertured portion which blocks communication between said chamber and a second plurality of upright passages, conduit means leading to said chamber for supplying $CO_2$-containing air, said baffle plate being constructed and arranged such that said air passes from said chamber through said apertures in said baffle plate into said first plurality of upright passages, said air passing upwardly in said first plurality of upright passages and subsequently being directed generally laterally by said upper support means such that the air then passes downwardly in said second plurality of upright passages to subsequently again be directed generally laterally by said non-apertured portion of said baffle plate to once again pass upwardly in said first plurality of upright passages, whereby the air circulates in said bath means between said tubular photoradiators.

25. An apparatus as claimed in claim 9, in which each of the apertures has a diameter which allows a culture medium to pass therethrough, the conduit means being communicable to a vacuum source during collection of the product of photosynthesis.

26. An apparatus as claimed in claim 24, in which each of the apertures has a diameter which passes the air while blocking a culture medium.

27. An apparatus as claimed in claim 24 further comprising check valve means for preventing a culture medium from dropping through the apertures while permitting the air to pass therethrough.

28. An apparatus as claimed in claim 27, in which the check valve means comprises an upwardly tapered bore which is defined by each of the apertures.

29. An apparatus as claimed in claim 27, in which the check valve means comprises an upwardly tapered bore which is defined by each of the apertures, a valve seat member screwed into the lower end of the tapered bore and a ball movably seated on said valve seat member inside the tapered bore.

30. Apparatus for photosynthesis comprising bath means containing a photosynthetic reaction bath, a plurality of tubular photoradiators arranged upright in said bath means in parallel array, upper support means and lower support means in said bath means for supporting the upper and lower end portions respectively of said tubular photoradiators, said tubular photoradiators being spaced from one another so as to define a plurality of upright passages between said tubular photoradiators, said upper support means closing off the upper ends of said upright passages, said lower support means comprising a plurality of tubes having an axial length shorter than the axial length of said tubular photoradiators, bonding means bonding said tubes to one another, said tubular photoradiators having lower end portions fitted fluid-tightly to the insides of said tubes, said upright passages each having a lower portion and an upper portion, said lower portion being defined by said tubes, said upper portions being defined by said tubular photoradiators, a baffle plate contacting the underside of said lower support means, said bath means having a lower chamber underlying said baffle plate, said baffle plate having a plurality of apertures providing communication between said chamber and a first plurality of upright passages, said baffle plate having a non-apertured portion which blocks communication between said chamber and a second plurality of upright passages, conduit means leading to said chamber for supplying $CO_2$-containing air, said baffle plate being constructed and arranged such that said air passes from said chamber through said apertures in said baffle plate into said first plurality of upright passages, said air passing upwardly in said first plurality of upright passages and subsequently being directed generally laterally by said upper support means such that the air then passes downwardly in said second plurality of upright passages to subsequently again be directed generally laterally by said nonapertured portion of said baffle plate to once again pass upwardly in said first plurality of upright passages, whereby the air circulates in said bath means between said tubular photoradiators.

31. Apparatus for photosynthesis comprising bath means containing a photosynthetic reaction bath, a plurality of tubular photoradiators arranged upright in said bath means in parallel array, upper support means and lower support means in said bath means for supporting the upper and lower end portions respectively of said tubular photoradiators, said tubular photoradiators being disposed so as to define a plurality of upright passages between said tubular photoradiators, said upper support means closing off the upper ends of said upright passages, a baffle plate underlying said lower support means, said baffle plate being spaced from said lower support means to define an intermediate space therebetween, said bath means having a lower chamber underlying said baffle plate, said baffle plate having a plurality of apertures generally vertically aligned with a first plurality of upright passages, said baffle plate having a non-apertured portion underlying a second plurality of upright passages, conduit means leading to said chamber for supplying $CO_2$-containing air, said baffle plate being constructed and arranged such that said air passes from said chamber through said apertures in said baffle plate into said first plurality of upright passages via said intermediate space, said air passing upwardly in said first plurality of upright passages and subsequently being directed generally laterally by said upper support means such that the air then passes downwardly in said second plurality of upright passages, at least some of said downwardly moving air in said second plurality of upright passages passing into said intermediate space to subsequently again be directed generally laterally in said intermediate space by said non-apertured portion of said baffle plate to once again pass upwardly in said first plurality of upright passages, whereby the air circulates in said bath means.

32. An apparatus as claimed in claim 31, wherein said tubular photoradiators are in contact with one another, said tubular photoradiators each having a smaller diameter at its upper end relative to the diameter at its lower end.

33. Apparatus for photosynthesis comprising bath means containing a photosynthetic reaction bath, a plurality of tubular photoradiators arranged upright in said bath means in parallel array, upper support means and lower support means in said bath means for supporting the upper and lower end portions respectively of said tubular photoradiators, said tubular photoradiators being spaced from one another so as to define a plurality of upright passages between said tubular photoradiators, said upper support means closing off the upper ends of said upright passages, said bath means having a lower chamber underlying said lower support means, said lower support means having a flow-through portion which provides communication between said chamber and a first plurality of upright passages and a stopped-up portion which blocks communication between said chamber and a second plurality of upright passages, conduit means leading to said chamber for supplying $CO_2$-containing air, said flow-through portion and said stopped-up portion of said lower support means being constructed and arranged such that said air passes from said chamber through said flow-through portion into said first plurality of upright passages, said air passing upwardly in said first plurality of upright passages and subsequently being directed generally laterally by said upper support means such that the air then passes downwardly in said second plurality of upright passages to subsequently again be directed generally laterally by said stopped-up portion of said lower support means to once again pass upwardly in said first plurality of upright passages, whereby the air circulates in said bath means between said tubular photoradiators, circulation means disposed in said lower chamber for causing the air to circulate along a variable path in said bath means and for varying the pressure distribution of said air in a bottom portion of said bath means, said conduit means having an extension which projects into said lower chamber, said circulation means comprising a rotor rotatably coupled over said extension, said rotor having ejection ports, said rotor receiving said air from said conduit means and ejecting air from said ejection ports to thereby supply said air into said bath means during rotation thereof.

34. An apparatus as claimed in 33 in which the bath means has a polygonal cross-section, the rotor further comprising air ejection ports which are respectively open radially outwardly of the rotor.

* * * * *